United States Patent
Ivkov et al.

(10) Patent No.: US 9,333,369 B2
(45) Date of Patent: May 10, 2016

(54) SYSTEMS AND METHODS TO REDUCE POWER DEPOSITION IN TISSUE EXPOSED TO RADIO FREQUENCY ELECTROMAGNETIC FIELDS

(75) Inventors: Robert Ivkov, Ellicott City, MD (US); Ananda Kumar, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 827 days.

(21) Appl. No.: 13/503,520

(22) PCT Filed: Oct. 22, 2010

(86) PCT No.: PCT/US2010/053801
§ 371 (c)(1),
(2), (4) Date: Jun. 22, 2012

(87) PCT Pub. No.: WO2011/050290
PCT Pub. Date: Apr. 28, 2011

(65) Prior Publication Data
US 2012/0265000 A1  Oct. 18, 2012

Related U.S. Application Data

(60) Provisional application No. 61/253,869, filed on Oct. 22, 2009.

(51) Int. Cl.
*A61N 2/02* (2006.01)
*A61B 5/055* (2006.01)
*A61B 5/00* (2006.01)
(Continued)

(52) U.S. Cl.
CPC . *A61N 2/02* (2013.01); *A61B 5/055* (2013.01); *A61B 5/416* (2013.01); *A61N 1/403* (2013.01); *G01R 33/422* (2013.01)

(58) Field of Classification Search
CPC ........... A61N 2/02; A61N 2/12; A61N 1/403; A61B 5/005; A61B 5/416; G01R 33/422
USPC ....................................................... 600/10, 15
See application file for complete search history.

(56) References Cited

U.S. PATENT DOCUMENTS 4,873,995 A * 10/1989 Kikuchi et al. ............... 607/102
6,074,385 A *  6/2000 Klopotek ......................... 606/27
(Continued)

OTHER PUBLICATIONS

Deng et al. "Capacity Evaluation of a MEMS Based Micro Cooling Device Using Liquid Metal as Coolant" Proceedings of the 1st IEEE International Conference on Nano/Micro Engineered and Molecular Systems, Jan. 2006.*
(Continued)

*Primary Examiner* — Navin Natnithithadha
*Assistant Examiner* — Kaylee Wilson
(74) *Attorney, Agent, or Firm* — Johns Hopkins Technology Ventures

(57) ABSTRACT

An apparatus for exposing a region of interest of an object, animal or person to an alternating magnetic field has a source of radio-frequency electromagnetic radiation arranged to provide the alternating magnetic field in an exposure volume defined by the apparatus, and a shield arranged between the source of radio-frequency electromagnetic radiation and the exposure volume. The shield includes a material that has a sufficient thickness and arrangement to reduce power deposition to at least regions outside of the region of interest of the object, animal or person during exposure in the exposure volume.

13 Claims, 10 Drawing Sheets

(51) Int. Cl.
*A61N 1/40* (2006.01)
*G01R 33/422* (2006.01)

(56) References Cited

U.S. PATENT DOCUMENTS

| | | | |
|---|---|---|---|
| 6,235,251 B1 | 5/2001 | Davidson | |
| 2003/0028071 A1 | 2/2003 | Handy et al. | |
| 2004/0044385 A1 | 3/2004 | Fenn et al. | |
| 2004/0044386 A1* | 3/2004 | Beens et al. | 607/101 |
| 2008/0097141 A1* | 4/2008 | Kolt | A61N 2/02 600/13 |
| 2008/0249350 A1* | 10/2008 | Marchitto et al. | 600/10 |

OTHER PUBLICATIONS

Horsman, et al., Hyperthermia: a potent enhancer of radiotherapy, Clinical Oncology (2007) 19, pp. 418-426.
Roti Roti, Heat-induced alterations of nuclear protein associations and their effects on DNA repair and replication, Int. J. Hypertherimia, (2007) 23, pp. 3-15.
Hunt, et al., Hyperthermia activates a subset of ataxia-telangiectasia mutated effectors independent of DNA strand breaks and heat shock protein 70 status, Cancer Res., (2007) 67, pp. 3010-3017.
Dewhirst, et al., Intl. J. Hyperthermia (2003) 19, pp. 267-294.
Van Der Zee, Heating the patient: A promising approach? Annals of Oncology 2002, 13, 1173-1184.
Adair, et al., Thermoregulatory responses to RF energy aborption Bioelectromagnetics Supplement (2003), 6, S17-S38.
Liu, et al., On the induced electric field gradients in the human body for magnetic stimulation by gradient coils in MRI, IEEE Trans. on Biomedical Engineering (2003) 50, pp. 804-815.
Hagman, et al., Numerical calculation of electromagnetic energy deposition for a realistic model of man, IEEE Trans. Microwave Theory and Technol., (1979) 27, p. 804.
Candeo, et al., Numerical FEM models for the planning of magnetic induction hyperthermia treatments with nanoparticles, IEEE Trans, on Magnetics (2009) 45, pp. 1658-1661.
Denardo, et al., Thermal dosimetry predictive of efficacy of I I IIn-ChL6 nanoparticle AMF-induced thermoablative therapy for human breast cancer in mice, J. Nuc. Med, (2007) 48, pp. 437-444.
Stauffer, et al., Practical induction heating coil designs for clinical hyperthermia with ferromagnetic implants, IEEE Transactions on Biomedical Engineering, (1994) 41, pp. 17-28).
Dennis, et al., Nearly complete regression of tumors via collective behavior of magnetic nanoparticles in hyperthermia, Nanotechnology (2009) 20, pp. 395103.
Rosensweig, Heating magnetic fluid with alternating magnetic field, J. Magnetism and Magn. Materials, (2002) 252, pp. 370-374.
Trakic, et al., Transient temperature rise in a mouse due to low-frequency regional hyperthermia, Phys. Med. and Biol , (2006) 51, pp. 1673-1691.
Ivkov, et al., Application of high amplitude alternating magnetic fields for heat induction of nanoparticles localized in cancer, Clin. Cancer Res. (2005) 11(19 Suppl), pp. 7093s-7103s.

* cited by examiner

SYSTEMS AND METHODS TO REDUCE POWER DEPOSITION IN TISSUE EXPOSED TO RADIO FREQUENCY ELECTROMAGNETIC FIELDS

CROSS-REFERENCE TO RELATED APPLICATIONS

This application is a 35 U.S.C. §371 U.S. national entry of International Application PCT/US2010/053801 having an international filing date of Oct. 22, 2010, which claims the benefit of U.S. Provisional Application No. 61/253,869, filed Oct. 22, 2009, the content of each of the aforementioned applications is herein incorporated by reference in their entirety.

BACKGROUND

1. Field of Invention

The field of the current invention relates to an apparatus, method and system for exposing a region of interest of an object, animal or person to an alternating magnetic field.

2. Discussion of Related Art

The use of radiofrequency (RF) electromagnetic fields has many applications in biology and medicine, for example. Among these are hyperthermia treatments for cancer, and other diseases and ailments, and for imaging tissues such as in magnetic resonance imaging (MRI). RF fields used for hyperthermia cancer treatment and high-field magnetic resonance imaging expose tissues to high amplitude fields with frequencies of 50 kHz-20 MHz for a period of time. For hyperthermia treatment the intent is to selectively heat cancer tissue to damage and kill cancer cells, or to sensitize cancer cells to the effects of radiation and anti-cancer drugs. Alternating magnetic fields (AMF) in the radiofrequency spectrum can be used to localize heat by heating antigen-targeted magnetic nanoparticles in the cancer tissue. For MRI, the tissue exposure of RF results from and depends upon the nature of activation of the imaging sequences of high field MRI devices. In both cases, direct tissue heating results from interaction of AMF with tissue. For cancer hyperthermia the challenge is to minimize this non-specific power deposition over large regions of tissue to avoid overheating and damaging or killing normal surrounding tissue.

It has been established that the application of heat for cancer therapy has significant potential, particularly when used in combination with radiation. The profound effect of heat on cancer cells is largely due to the physical environment of the tumor, and not necessarily because cancer cells are intrinsically more sensitive to heat. However, cancer cells generally possess more limited recovery capabilities than their normal counterparts contributing to the overall increased susceptibility to heat. Chronic hypoxia, low pH, chaotic vascularity, and nutritional deprivation characterize the interior of many tumors that consequently increases the sensitivity of cells to heat. In addition, mammalian cells are most sensitive to effects of heat and radiation at different stages of the mitotic cycle, further enhancing the potential therapeutic effects of the combination. (M. R. Horsman, J. Overgarrd; Hyperthermia: a potent enhancer of radiotherapy, *Clinical Oncology* (2007) 19, pp. 418-426; M. W. Dewhirst, E. Jones, T. Samulski, Z. Vujaskovic, C. Li, L. Prosnitz in *Cancer Medicine*, D. W. Kufe, R. E. Pollock, R. R. Weichselbaum, R. C. Bast, Jr., T. S. Gansler, Eds., (B C Decker, Hamilton, ed. 6, (2003) pp. 623-636. (sixth edition); J. L. Roti Roti, Heat-induced alterations of nuclear protein associations and their effects on DNA repair and replication, *Int. J. Hyperthermia*, (2008) 23, pp. 3-15; C. R. Hunt, R. K. Pandita, A. Laszlo, et al., Hyperthermia activates a subset of ataxia-telangiectasia mutated effectors independent of DNA strand breaks and heat shock protein 70 status, *Cancer Res.*, (2007) 67, pp. 3010-3017).

It is believed that the beneficial effects of hyperthermia for cancer can only be realized if a therapeutic temperature (42° C. to 46° C.) is achieved and maintained for a sufficient period of time throughout the tumor (Dewhirst et al., Supra; M. W. Dewhirst, B. L. Viglianti, M. Lora-Michiels, M. Hanson, P. J. Hoopes, *Intl. J. Hyperthermia* (2003) 19, pp. 267-294). Generally, higher temperatures produce greater effects. Similar effects are observed with increased time of exposure. These requirements present technical challenges because the heating must occur while simultaneously minimizing heat deposition to the surrounding normal tissue. The combination of these challenges and other factors has inhibited widespread application of this tool in the clinical setting (Dewhirst et al., *Cancer Medicine, Supra*; J. van der Zee, Heating the patient: A promising approach? *Annals of Oncology* 2002, 13, 1173-1184).

These barriers become particularly challenging when attempting to address metastatic cancer, such as metastatic prostate cancer. Characteristic of metastatic disease is the widespread appearance of deep-tissue (>7 cm) tumors in many organs and bone. Many techniques and devices that have been developed to heat tissue deliver electromagnetic ("EM") radiation in the radio- or microwave frequencies to a selected region of the body. The heat dose thus depends upon the interaction of time-varying electromagnetic fields with tissues, and upon the time of treatment. The manner of the tissue-EM interaction and resulting power or heat deposition from electromagnetic fields strongly depends upon the frequency of the EM field, and the dielectric permittivity and electrical conductivity of tissue(s) (C. Polk, Introduction in *Biological and Medical Aspects of Electromagnetic Fields, Third Edition*; Eds. F. S. Barnes and B. Greenebaum, CRC Press, Taylor & Francis Group, Boca Raton, Fla., (2006) pp. xiii-xxvi; U. Cerchiari, Hyperthermia, physics, vector potential, electromagnetic heating: A primer in *Hyperthermia in Cancer Treatment: A primer*, Eds. G. F. Baronzio and E. D. Hager, Landes Bioscience and Springer, New York, N.Y. (2006), pp. 3-18; A. Szasz, O. Szasz, N. Szasz, Physical background and technical realizations of hyperthermia in *Hyperthermia in Cancer Treatment: A primer*, Eds. G. F. Baronzio and E. D. Hager, Landes Bioscience and Springer, New York, N.Y. (2006), pp. 27-52; E. R. Adair, D. R. Black, Thermoregulatory responses to RF energy aborption *Bioelectromagnetics Supplement* (2003), 6, S17-S38). In biological tissue with finite conductivity σ (S/m) the electric field $\vec{E}$ (V/m) induces a current, $\vec{I}=\sigma\vec{E}$, that deposits power in the tissue via joule heating. The power deposited to the tissue is defined as the specific absorption rate (SAR) given by $$SAR = \frac{\sigma|\vec{E}|^2}{\rho_{+n}} \quad (1)$$

where, $\rho_m$ is the mass density of tissue in (kg/m³) (Szasz, et al., supra; F. Liu, H. Zhao, S. Crozier, On the induced electric field gradients in the human body for magnetic stimulation by gradient coils in MRI, *IEEE Trans. On Biomedical Engineering* (2003) 50, pp. 804-815).

It is difficult to control this heating because living tissue is a highly complex and responsive medium that contains layers of tissue differing in composition and density, comprises a fractal network of blood vessels that transport heat, and harbors multiple interfacial regions that can reflect, scatter, or absorb EM waves. Reflection and transmission of EM waves impinging a planar tissue interface are determined by the properties of the EM waves and tissue, and by the geometry of the interaction (M. J. Hagman, O. P. Gandhi, C. H. Durney, Numerical calculation of electromagnetic energy deposition for a realistic model of man, *IEEE Trans. Microwave Theory and Technol.*, (1979) 27, p 804; Liu, et al., supra). These effects place demands on technological innovation thus limiting the successful translation into clinical settings.

High frequency electric fields are strongly attenuated by soft tissue and bone, the latter having a particularly strong effect. Conversely, low frequency magnetic fields, i.e. 100-300 kHz, are not significantly attenuated by tissue, even bone, making this an attractive mode for metastatic disease therapy. Low frequency fields heat tissue by capacitive and magnetic induction; however, they cannot discriminate normal tissue from tumors (Szasz, et al., supra).

Coupling low-frequency energy with magnetic materials concentrated in the target region offers more precise and selective heat deposition by providing a susceptive material in the cancer tissue that efficiently couples with the electromagnetic energy. And, this approach simultaneously avoids the interference to power absorption caused by bone and boundaries occurring at the interface of tissues with varying conductivities (A. Candeo, F. Dughiero, Numerical FEM models for the planning of magnetic induction hyperthermia treatments with nanoparticles, *IEEE Trans. on Magnetics* (2009) 45, pp. 1658-1661; A. Jordan, P. Wust, R. Scholz, H. Faehling, J. Krause, R. Felix, Magnetic fluid hyperthermia (MFH), *Scientific and Clinical Applications of Magnetic Carriers*, Eds. U. Häfeli, M. Zborowski, W. Schütt, Plenum Press, New York, N.Y. (1997), pp. 569-595). Recent efforts have demonstrated the potential to selectively heat tumors with biocompatible magnetic nanoparticle suspensions or ferrofluids exposed to external alternating magnetic fields (S. J. DeNardo, G. L. DeNardo, A. Natarajan, L. A. Miers, A. R. Foreman, C. Gruettner, G. N. Adamson, R. Ivkov, Thermal dosimetry predictive of efficacy of 111In-ChL6 nanoparticle AMF-induced thermoablative therapy for human breast cancer in mice, *J. Nuc. Med.*, (2007) 48, pp. 437-444). Induction heating techniques and equipment are most applicable for this approach to thermal therapy, with particular emphasis on the design and manufacture of induction coils (P. R. Stauffer, P. K. Sneed, H. Hashemi, T. L. Phillips, Practical induction heating coil designs for clinical hyperthermia with ferromagnetic implants, *IEEE Transactions on Biomedical Engineering*, (1994) 41, pp. 17-28).

The magnetic particles are nano-scale susceptors that generate heat via several potential mechanisms when exposed to the externally applied AMF (C. L. Dennis, A. J. Jackson, J. A. Borchers, P. J. Hoopes, R. Strawbridge, A. R. Foreman, J. van Lierop, C. Grüttner, R. Ivkov, Nearly complete regression of tumors via collective behavior of magnetic nanoparticles in hyperthermia, *Nanotechnology* (2009) 20, pp. 395103; R. E. Rosensweig, Heating magnetic fluid with alternating magnetic field, *J. Magnetism and Magn. Materials*, (2002) 252, pp. 370-374; Jordan, et al., supra). The amount of heat deposited in a volume of tissue, D (Joules/g tissue) at fixed frequency, is proportional to the tissue particle concentration, Π (g particle/g tissue), the AMF-amplitude dependant power loss function of the particles, Ψ(H) (Watts/g particle), the amplitude of magnetic field, H (Amperes/m), and total treatment time, t (seconds) (DeNardo, et al., supra):

$$D = \Pi \times \Psi(H) \times H \times t. \quad (2)$$

Additional heat may result from the magnetic dipole interactions of the particles that result from an inhomogeneous distribution within the tumor and around cells (Dennis, et al., supra). The additional heating resulting from this mechanism may contribute significantly to the potential success of this treatment (Dennis, et al., supra; Candeo, et al., supra).

The characteristics of low-frequency EM field interactions with the biological tissue are: (1) the E-fields are concentrated at the surface of the biological body, and perpendicular to the surface, (2) E- and H-fields are decoupled inside a biological body, (3) the E-fields are weakened by a large dielectric permittivity upon penetration into biological tissues, (4) the magnetically induced E-field encircles the H-field and produces eddy currents with a magnitude that increases with distance from the center of the body, and (5) an eddy current appears in each region inside the body with a different conductivity and behaves as a unit with its own body center and radius or equivalent radius (F. S. Barnes, B. Greenbaum, Bioengineering and Biophysical Aspects of EM Fields, pp. 298-297; Liu, et al., supra; A. Trakic, F. Liu, S. Crozier, Transient temperature rise in a mouse due to low-frequency regional hyperthermia, *Phys. Med. and Biol.*, (2006) 51, pp. 1673-1691).

Interactions of low-frequency E-fields with magnetic nanoparticles provide little contribution to therapeutic heating effects, and thus are considered irrelevant in the current context. In contrast, optimizing the B-field interaction with magnetic particles by increasing both amplitude and improving the geometry of interaction is desired to maximize the heat produced in the target tissue. However, non-specific heat is also deposited via tissue coupling with the B-field component of EM fields through magnetic induction, or production of eddy currents. The heat deposited, or the SAR, by this process is proportional to tissue conductivity, and EM parameters:

$$SAR \propto \sigma \times f^2 \times H^2 \times r^2, \quad (3)$$

where f is frequency of AMF in Herz (Hz), and r is radius of the exposed tissue region. Increasing the heat dose deposited by the particles at constant frequency for a given particle concentration can be accomplished by increasing the AMF amplitude (Equation 2), which also increases eddy current heating and SAR (Equation 3) (R. Ivkov, S. J. DeNardo, W. Daum, A. R. Foreman, R. C. Goldstein, V. S. Nemkov, G. L. DeNardo, Application of high amplitude alternating magnetic fields for heat induction of nanoparticles localized in cancer, *Clin. Cancer Res.* (2005) 11(19 Suppl), pp. 7093s-7103s). Therefore, it becomes a challenging compromise to maximize the heat output of the particles by increasing the AMF amplitude homogeneously over a large region of interest (ROI) at a select frequency of AMF without depositing excessive power in normal tissue. There thus remains a need for improved systems to expose ROI's of an object to high amplitude AMF while decreasing the amount of heating in regions around the ROI's.

SUMMARY

An apparatus for exposing a region of interest of an object, animal or person to an alternating magnetic field according to some embodiments of the current invention has a source of radio-frequency electromagnetic radiation arranged to provide the alternating magnetic field in an exposure volume defined by the apparatus, and a shield arranged between the source of radio-frequency electromagnetic radiation and the exposure volume. The shield includes a material that has a sufficient thickness and arrangement to reduce power deposition to at least regions outside of the region of interest of the object, animal or person during exposure in the exposure volume.

A system for heating localized regions within a body according to some embodiments of the current invention has a source of radio-frequency electromagnetic radiation arranged to provide an alternating magnetic field in an exposure volume defined by the system; a shield arranged between the source of radio-frequency electromagnetic radiation and the exposure volume; and a plurality of magnetic particles that are suitable to be disposed in the body. The shield includes a material that has a sufficient thickness and arrangement to attenuate electric field components of the electromagnetic radiation produced by the source by a predetermined amount prior to reaching the exposure volume while permitting magnetic field components of the electromagnetic radiation to pass through with less attenuation than the attenuation of the electric field components, and the alternating magnetic field in the exposure volume is suitable to interact with the magnetic particles to generate a predetermined amount of heat.

A method of exposing a region of interest of an object, animal or person to an alternating magnetic field according to some embodiments of the current invention includes generating electromagnetic radiation having a predetermined frequency and amplitude; arranging the object, animal or person to be exposed to at least an alternating magnetic field component of the electromagnetic radiation; and arranging a shield such that it reduces power deposition to regions outside of the region of interest of the object, animal or person when being exposed to the alternating magnetic field.

BRIEF DESCRIPTION OF THE DRAWINGS

Further objectives and advantages will become apparent from a consideration of the description, drawings, and examples.

DETAILED DESCRIPTION

Figure 1A:
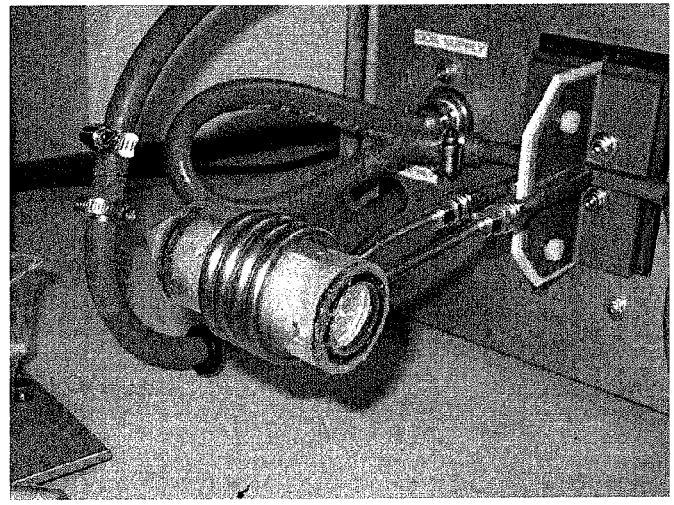
FIG. 1A is a photograph of an apparatus for exposing a region of interest of an object, animal or person to an alternating magnetic field (AMF) according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Because a significant contribution to the non-specific heating (SAR) results from the induced motion of charges in the tissue in response to the varying electric field, we hypothesize that the SAR can be reduced by introducing dielectric shielding around the sample volume to minimize the interaction of tissue with electric (E) fields. However, the concepts of the current invention are not limited to whether our hypothesis regarding the dielectric properties of the shield are correct. As long as the shielding material is effective for the particular application, the invention is not limited to the correctness of the theory of the mechanism. According to some embodiments of the current invention, our aim is to maintain high AMF amplitudes over a large region of interest (ROI) at a select frequency of AMF, to induce heating of the magnetic nanoparticles at the tumor site, without depositing excessive power in normal surrounding tissue regions. One solution to this challenge may be achieved with a dielectric material, or material having necessary heat transfer and electromagnetic properties to shield the electric fields to minimize the power deposition that cause non-specific heating, for example. Water was found to be a suitable material according to some embodiments of the current invention. Water was selected as a shielding material according to an embodiment of the current invention because it has a high dielectric constant (80.10), has high specific heat and conductivity, and is diamagnetic, and nearly transparent to magnetic fields. Heavy water, which contains deuterium in place of hydrogen atoms, was also found to be a suitable material, although it may not be as effective as light (or normal) water. This could call into question our understanding of the underlying mechanism, but, irrespective of the theory of the mechanism of operation, water, and for some applications, heavy water, were found to be suitable shielding materials according to some embodiments of the current invention.

In some examples, we present results obtained from computer simulations, gel phantoms, and mouse models that demonstrate a two-fold reduction of the non-specific heating. Further reductions of non-specific heating were obtained by flowing the water through the shield for active cooling. These results demonstrate the potential value of water to permit high AMF amplitudes at tumor sites to activate the magnetic nanoparticle heating while controlling overall heating in normal tissues.

Figure 1B:
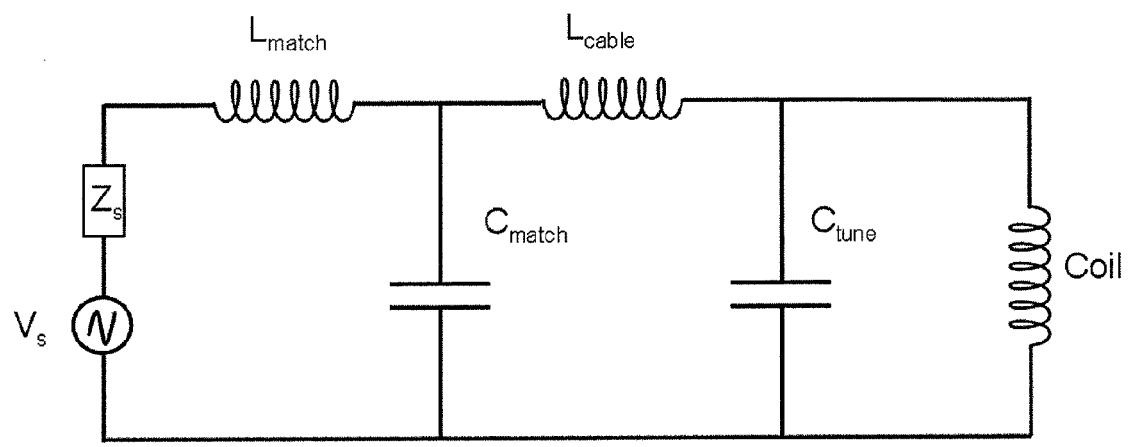
FIG. 1B is a circuit diagram of the AMF system corresponding to the example of FIG. 1A.
Figure 1C:
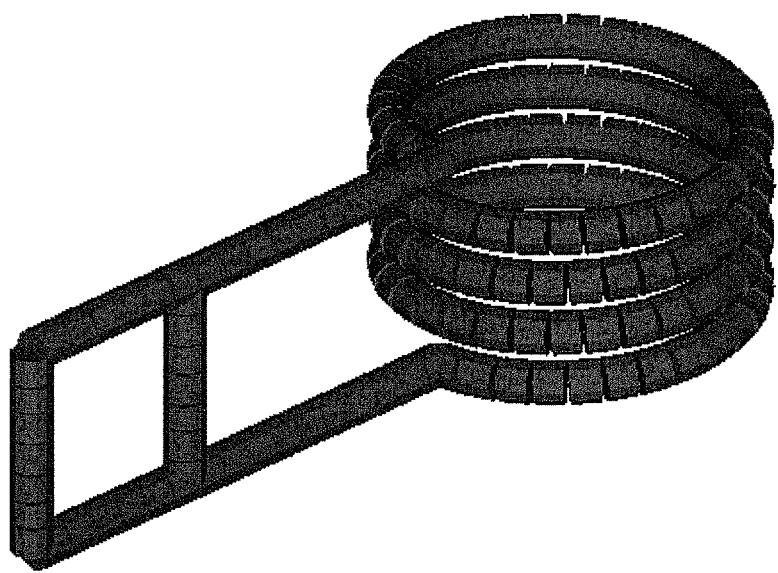
FIG. 1C illustrates a four turn solenoid coil modeled using Method of Moments (MoM). The coil inner diameter (id) is 45 mm and coil length is 32 mm.

FIG. 1A shows an example of an apparatus for exposing a region of interest of an object, animal or person to an alternating magnetic field according to an embodiment of the current invention. Data were taken using this device and presented in the examples, below. In this example, the solenoid coil has four turns. FIG. 1B is a circuit diagram corresponding to this example. FIG. 1C illustrates the four turn solenoid coil modeled using Method of Moments (MoM). The coil inner diameter (id) is 45 mm and coil length is 32 mm.

Figure 1D:
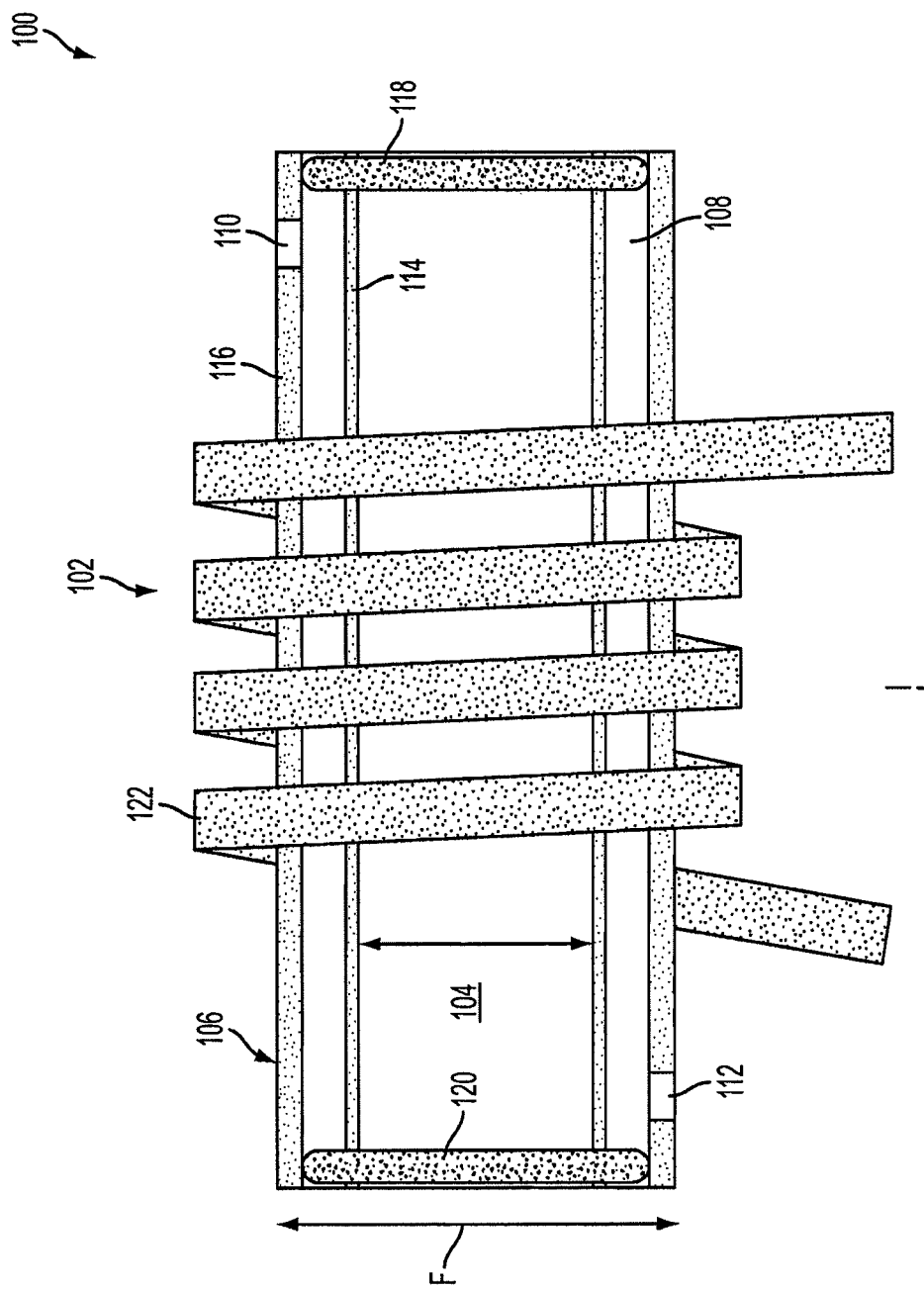
FIG. 1D is a schematic illustration of an apparatus for exposing a region of interest of an object, animal or person to an alternating magnetic field (AMF) according to an embodiment of the current invention.

FIG. 1D is a schematic illustration of an apparatus 100 for exposing a region of interest of an object, animal or person to an alternating magnetic field according to an embodiment of the current invention. Although many applications of the apparatus 100 may be directed to animals or humans for therapeutic heating effects, or for imaging, for example, the broad concepts of the current invention are not limited to only these examples. Other uses of the apparatus may be directed to objects other than animals or people. The apparatus 100 is a source of radio-frequency electromagnetic radiation 102 arranged to provide an alternating magnetic field in an exposure volume 104 defined by the apparatus 100, and a shield 106 arranged between the source of radio-frequency electromagnetic radiation 102 and the exposure volume 104. The shield 106 includes a material 108 that has a sufficient thickness and arrangement to reduce power deposition to at least regions outside of the region of interest of the object, animal or person during exposure in the exposure volume 104. In some embodiments, the material 108, structure and arrangement of the shield 106 are selected such that electric field components of the radio-frequency electromagnetic radiation are attenuated by a predetermined amount prior to reaching the exposure volume 104. In some embodiments, the material 108 can include a fluid. The material 108 can include light, heavy water, a liquid metal, metal particles suspended in the fluid or any combination thereof.

Figure 1E:
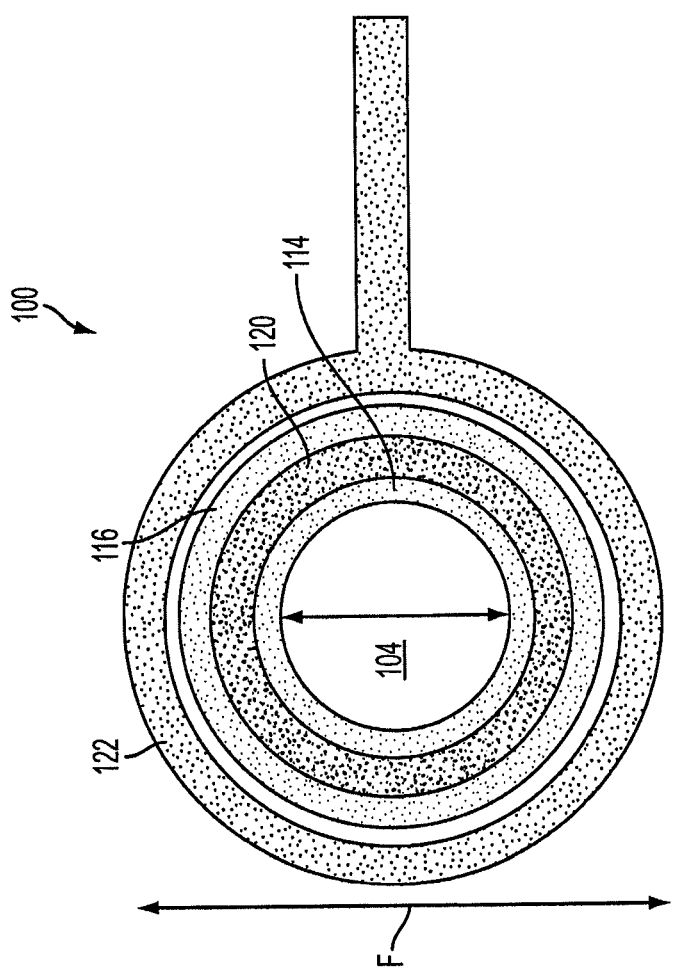
FIG. 1E is a side view corresponding to the example of FIG. 1D.
Figure 1F:
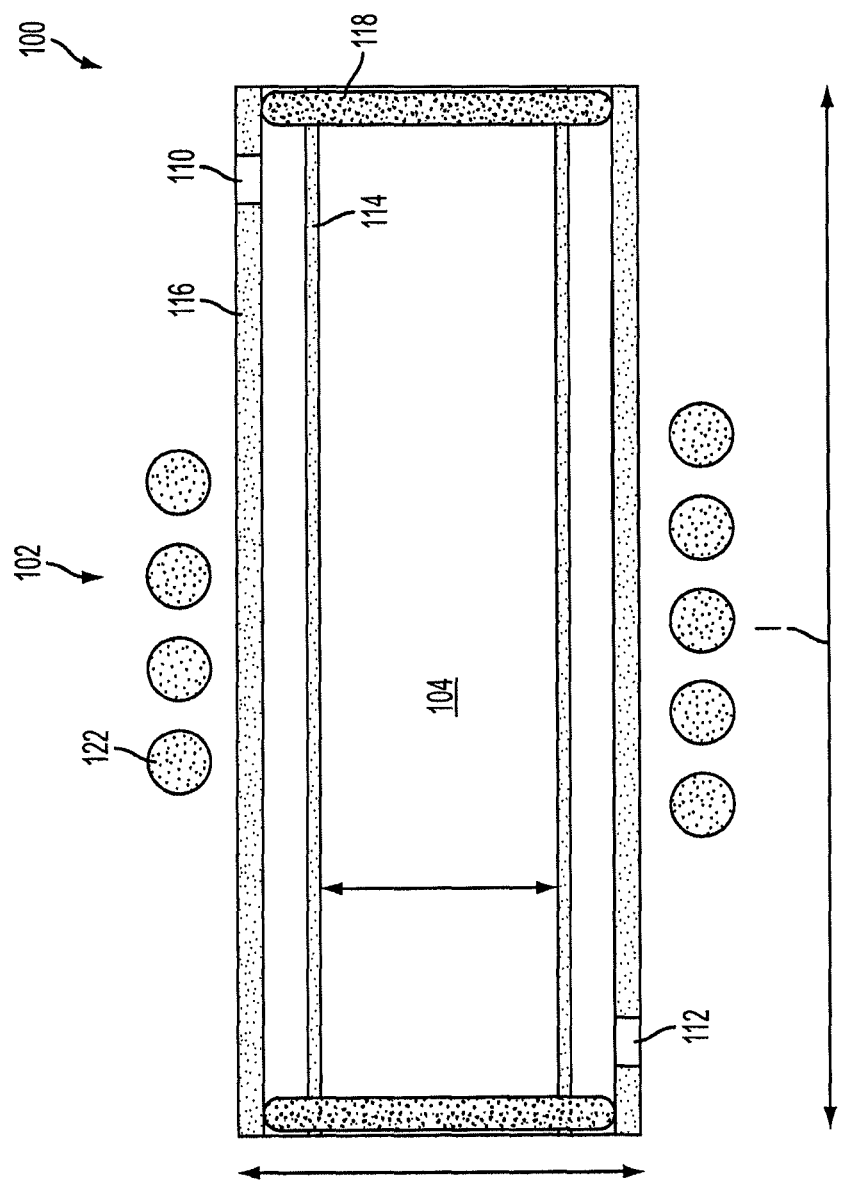
FIG. 1F is a cross-sectional view corresponding to the example of FIG. 1D.

In the embodiment of FIG. 1D, the shield 106 includes a fluid containment structure that has a first port 110 and a second port 112 such that fluid can be compelled to flow through said shield. For example, first port 110 can be an input port and second port 112 can be an output port, or vice versa, according to some embodiments of the current invention. Additional ports could be included, as desired. The shield 106 has an inner wall 114, an outer wall 116 and O-rings 118 and 120 arranged at opposing ends of the shield 106. FIG. 1E is an end view corresponding to FIG. 1D and FIG. 1F is a cross-sectional view corresponding to FIG. 1D. When water is used as the material 108, the thickness of the water layer can be selected according to the size of the apparatus, and correspondingly, the size of the object, person, or animal to be exposed to the AMF. For example, the water of said shield can be selected to have a thickness of at least about 2% of the inner diameter of inner wall 114 and less than about 20% of inner wall 114.

The source of radio-frequency electromagnetic radiation 102 can provide linearly polarized electric and magnetic fields having a frequency between 50 kHz and 1 MHz, and amplitude of between 10 kA/m and 1,000 kA/m according to some embodiments of the current invention. According to some embodiments, the source of radio-frequency electromagnetic radiation 102 includes an electrically conducting component 122 that winds around at least a portion of the exposure volume defined by the system to provide a solenoid. The source of radio-frequency electromagnetic radiation 102 also includes a power source, such as a voltage source, which is not shown in FIG. 1D-1F for clarity. The electrically conducting component 122 can be a metal coil according to some embodiments of the current invention. In some embodiments, electrically conducting component 122 can be metal tubing adapted to be connected to a cooling system to circulate coiling fluid through the metal tubing. This can permit the generation of higher power electromagnetic radiation without melting or otherwise damaging the source of radio-frequency electromagnetic radiation 102 and/or other components. According to some embodiments, the source of radio-frequency electromagnetic radiation 102 can be adapted to provide electromagnetic radiation with a frequency of at least 100 kHz. Electromagnetic radiation below 100 kHz can lead to problems with nerve stimulation and disruption of electronic components, for example. The source of radio-frequency electromagnetic radiation 102 can be adapted to provide electromagnetic radiation with a frequency between 100 kHz and 500 kHz. At frequencies higher than 500 kHz, extensive heating can occur. For some particular applications, the radio-frequency electromagnetic radiation 102 can be adapted to provide electromagnetic radiation with a frequency between 100 kHz and 300 kHz. For some applications, the radio-frequency electromagnetic radiation 102 can be adapted to provide electromagnetic radiation with a frequency between 130 kHz and 200 kHz. The source of radio-frequency electromagnetic radiation 102 can have an applied voltage of at least 500 V, for example.

A method of exposing a region of interest of an object, animal or person to an alternating magnetic field according to an embodiment of the current invention includes generating electromagnetic radiation having a predetermined frequency and amplitude; arranging the object, animal or person to be exposed to at least an alternating magnetic field component of the electromagnetic radiation; and arranging a shield such that it reduces power deposition to regions outside of the region of interest of the object, animal or person when being exposed to the alternating magnetic field.

A system for heating localized regions within a body according to an embodiment of the current invention can include an apparatus, such as apparatus 100, and a plurality of magnetic particles suitable to be disposed in the body to enhance localized heating.

EXAMPLES

In this study we demonstrate the effect of dielectric shielding by electromagnetic (EM) modeling and experiments in gel phantoms and mice. The results are compared with previous simulations (Trakic, et al., supra) and previously published results (Ivkov, et al., supra), and the model results are extended to predict the SAR reduction expected for a human-sized solenoid. For the studies described herein, the AMF frequency was 160 kHz generated by a four-turn solenoid coil. Agar gel phantoms having similar electrical conductivity to that of muscle at the chosen AMF frequency were used in the experimental validation with distilled water as the shielding material. We hypothesize that, due to its molecular asymmetry, polarity, and ability to hydrogen bond, water has the potential to control the field polarization and act as a shielding material for E-fields while maintaining nearly complete transparency to the B-fields. The simulation and gel phantom results are validated in mice to demonstrate the potential benefits in vivo.

Alternating Magnetic Field System

A system was designed and built according to an embodiment of the current invention to provide high-amplitude AMF in gel phantoms and a mouse. The system in this example comprises three main components; (a) the inductor coil, or inductor; (b) an external capacitance network that forms the resonant circuit in combination with the inductor (FIG. 1A); and (c) the power supply.

Inductor: The induction heating coil was a four-turn solenoid with inner diameter of 45.5 mm, outer diameter of 57.5 mm, and a length of 32 mm that was tuned to resonate at 160 kHz. It was constructed using dehydrated annealed soft-copper refrigerator tubing with 6.4 mm outer diameter (OD). To maintain the high electrical conductivity of the pre-annealed copper tubing, the coil was formed with a minimum of cold working. The interchangeable coil was connected to the capacitance or matching network with 10-mm diameter Swagelok brass tubing connectors to copper plates affixed to solid copper capacitance busses (FIG. 1A). Measurements of the AMF amplitude were taken in the center of the coil using a current probe capable to measure flux in two orthogonal dimensions. The current probe comprised two solenoids wound with Litz wire encased in a solid poly(vinyl) jacket (Fluxtrol, Inc., Auburn Hills, Mich.). The probe was calibrated to produce a potential that varied linearly with flux amplitude (peak-to-peak) in a range 4 kA/m to 65 kA/m, and frequency range 100 kHz to 800 kHz. The field amplitude was measured in the coil center before each set of trials. The measured amplitude in this point is reported as the experimental amplitude.

During operation, the inductor and all AMF components were cooled using a closed-loop, circulating water system maintained between 22° C. and 28° C. (Dry Cooler Systems, Inc., Auburn Hills, Mich.). The water system provides cooling from a 200-L reservoir with a flow rate of 100 L/min at 900 kPa. Stable oscillation at 160 kHz was achieved with tuned capacitors in the external tune/match box (Fluxtrol Inc., Auburn Hills, Mich.) as shown on FIG. 1A and the circuit diagram of the AMF system is shown on FIG. 1B.

Capacitance network and power supply: The external capacitance network (Fluxtrol, Inc., Auburn Hills, Mich.) was adjusted for stable oscillation at 159±1 kHz with a total capacitance of 1.33 µF with five 0.2 µF and one 0.33 µF capacitors, each rated to provide up to 400 A current at 1 kV. The coil and capacitance network are shown in FIG. 1A, and the circuit diagram of the AMF system is shown on FIG. 1B.

The power supply was an 80-kW induction heating system manufactured by PPECO (Watsonville, Calif.) that provides an alternating current to a resonant circuit with variable frequency between 135 kHz and 400 kHz. The power supply impedance was adjusted to match the coil and capacitance network by adjusting its internal inductance and capacitance. Matchbox and inductor electrical properties were measured using an LCR meter (QuadTec, Newton, Mass.).

Dielectric shield and mouse chamber: The mouse chamber was constructed from 50 ml conical centrifuge tubing having an inner diameter of 30 mm. Dielectric shielding was provided by distilled water contained in an Acrylic tube (inner diameter=38 mm and wall thickness~3.2 mm). To make the water cage device, two holes were drilled into the tube at opposite ends. Acrylic hose adapters (6 mm) were screwed into the holes with Teflon tape as a sealant. The 50-ml conical tube was suspended in the acrylic tube by two rubber O-rings at both ends of the tube. Adhesive silica-caulk was applied to ensure a water-tight seal at the ends of the acrylic tubing. For unshielded condition tests, no water was used in the acrylic tubing device. For the shielding condition, poly-acrylic tube was filled with distilled water (20° C.) from a closed-loop bench-top circulating bath (Hoefer Scientific Instruments, San Francisco, Calif.). Once filled, the pump was turned off to maintain a constant and still water level. For temperature-regulated measurements, the dielectric shield and mouse chamber was maintained at 35±0.5° C. by the bench-top circulating bath.

For all phantom and mouse experiments, temperatures were measured using three or four fiber optical temperature probes (FISO, Inc., Quebec, Canada). Temperatures were recorded at one-second intervals, beginning after phantoms or mice were in place for about thirty seconds before AMF exposure. For the mouse experiments, temperatures were measured from sham controls (no AMF power) for each shielding condition. These sham data were subtracted from experimental temperatures to correct for heating resulting from the 35° C. shielding water.

Numerical EM Simulations

Figure 2:
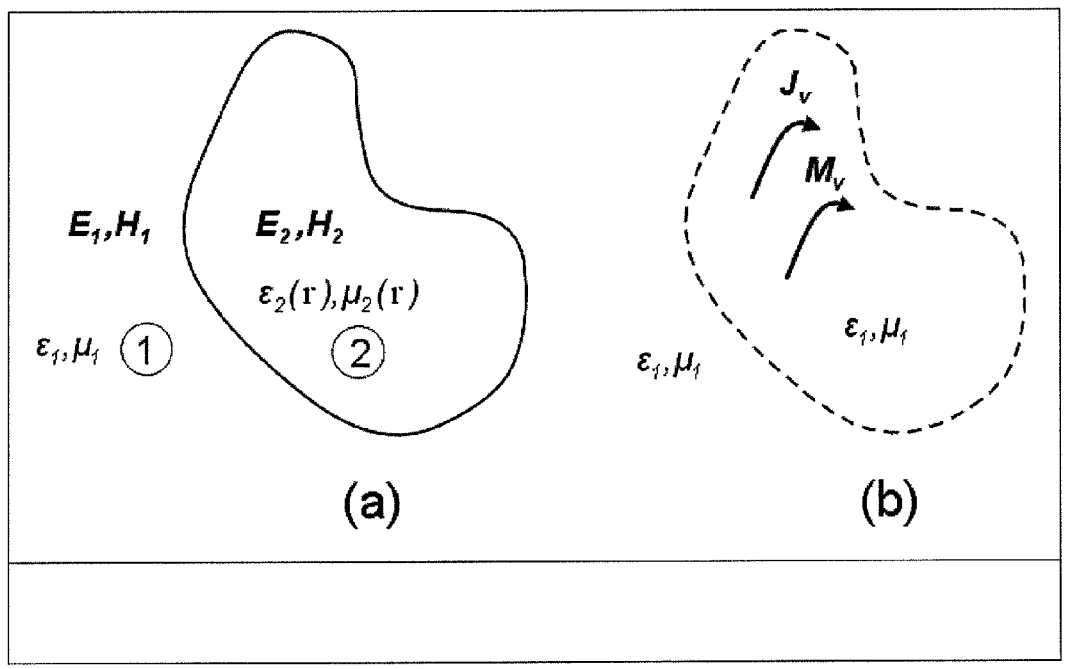
FIG. 2 illustrates a dielectric body in a homogeneous medium (a) original problem and (b) simplified to solve using MoM Volume Equivalence Principle (VEP).

The EM modeling and simulations used in this study were based on the Method of Moments (MoM) Volume Equivalence Principle (VEP). This method relies upon Friedholm integral equations of the second kind that are suited for low-frequency applications involving dielectric sample volumes (R. Harrington, *Field computation by method of moments*. New York: IEEE Press; 1993). The numerical field calculations employing MoM and VEP for biological media and applications have been used early on in the past (M. J. Hagman, O. P. Gandhi, C. H. Durney, Numerical calculation of electromagnetic energy deposition for a realistic model of man, *IEEE Trans. Microwave Theory and Technol.*, (1979) 27, p 804). In the MoM formulation involving VEP, a dielectric body with relative permittivity $\in_2$ and permeability $\mu_2$ is placed in a homogeneous medium with permittivity $\in_1$ and permeability $\mu_1$ as shown in FIG. 2. The material permittivity is complex in general and for simplicity two materials are considered here. The electric (E) and magnetic (H) fields at each point in space are superpositions of incident and scattered fields. The VEP transforms the problem described in FIG. 2(a) by introducing volume polarization electric and magnetic current densities given by $$\vec{J}_v(r) = j\omega[\in_2(r) - \in_r]\vec{E}(r) \tag{3}$$

$$\vec{M}_v(r) = j\omega[\mu_2(r) - \mu_r]\vec{H}(r) \tag{4}$$

The superposition of the impressed (subscript i) and the scattered (subscript s) fields are now expressed as, $$\vec{E} = \vec{E}_i + \vec{E}_s = \vec{E}_i + \mathfrak{I}_1^{J_v}\{\vec{J}_v\} + \mathfrak{I}_1^{M_v}\{\vec{M}_v\} \tag{5}$$

$$\vec{H} = \vec{H}_i + \vec{H}_s = \vec{H}_i + \eta_1^{J_v}\{\vec{J}_v\} + \eta_1^{M_v}\{\vec{M}_v\}. \tag{6}$$

Here $\mathfrak{I}$ and $\eta_1$ are three dimensional geometric operators. Eqns. (3-6), form a set of coupled integral equations for $\vec{J}_v$ and $\vec{M}_v$. These two volume-polarized current densities can be expressed in standard MoM formulation (Harrington, et al. supra) involving the superposition of a set of basis functions $\vec{f}_n^{J_v}$ and $\vec{f}_n^{J_v}$ with unknown expansion coefficients $\alpha_n^{J_v}$ and $\alpha_n^{M_v}$ as follows:

$$\vec{J}_v = \sum_{n=1}^{N} \alpha_n^{J_v} \vec{f}_n^{J_v} \text{ and } \vec{M}_v = \sum_{n=1}^{N} \alpha_n^{M_v} \vec{f}_n^{M_v}. \tag{7}$$

Using appropriate weighting functions to the integral equations typically employing Galerkin method (2) a system of linear equations are solved for the 3N unknowns. The number of cuboidal cells (N) used in the case of modeling the shielding medium and sample inside the mouse coil is 2849. For numerical stability of the solution, the maximum edge length of the cuboid cell is kept below 1.5 mm which is well below the quarter wavelength of fields inside the dielectric medium. A quad core processor (Intel) workstation (Sun 24, Palo Alto, Calif.) computer with 8 GB of RAM is used for the numerical calculations.

To demonstrate the validity of the application of MoM at the AMF frequency of interest, we first numerically calculate the solenoid coil inductance and compare it to the analytically calculated and experimentally measured values by an LCR meter.

Figure 3:
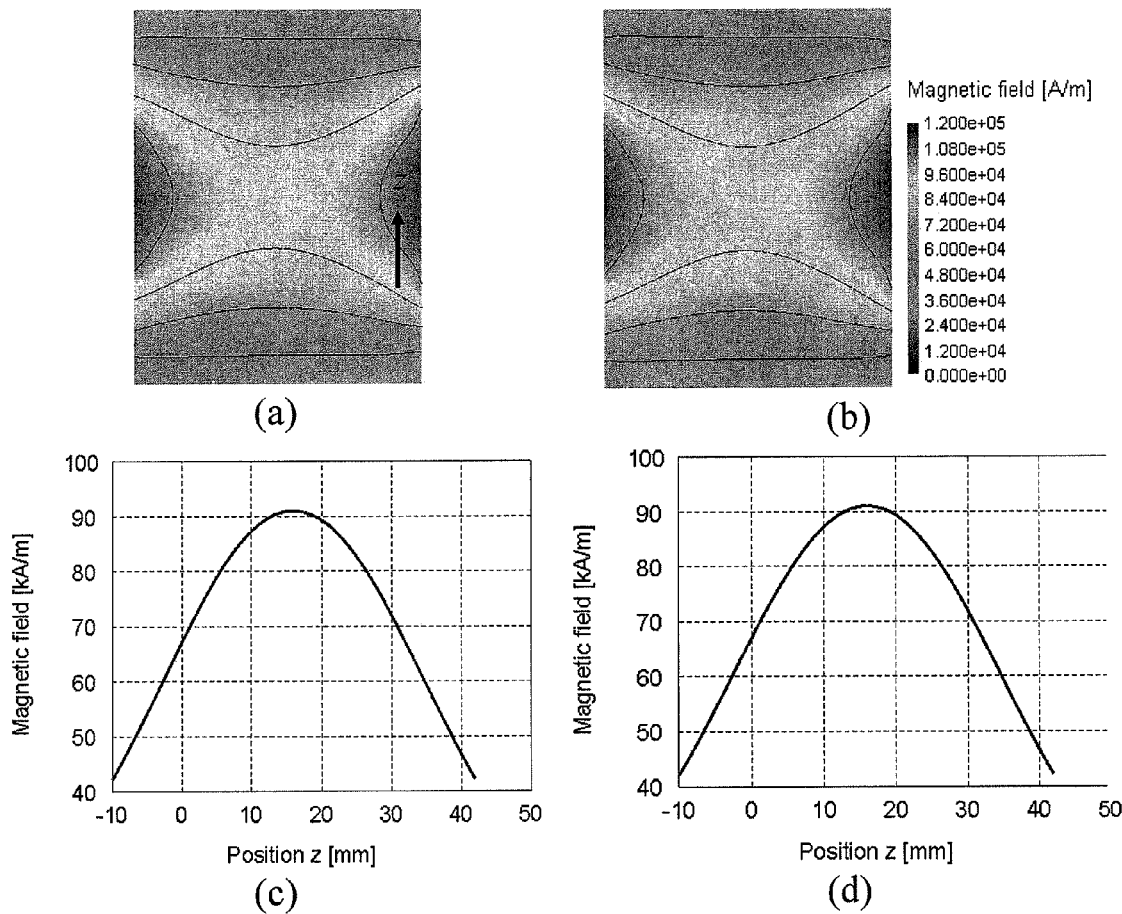
FIG. 3 shows the magnetic field across the (x-z plane) in the unshielded (a) and shielded (b) dielectric sample volume; Magnetic field profile along the middle of solenoid in z direction in unshielded (c) and shielded (d) sample volume for 8 kW (peak) input power to AMF coil.

The modeled solenoid coil and dielectric sample volume is shown in FIG. 3 below.

Analytical expression for determining inductance of the AMF coil is given below, $$L_{AMF} = L_S + 2L_1 - 2M_1 \quad (8)$$

where $L_S$ is the solenoid inductance, $L_1$ is the inductance of the lead wire extension from the tune box and $M_1$ is the mutual inductance between the parallel lead wire extension. The solenoid inductance is given by (N. Ida, *Engineering Electromagnetics*, 2nd edition, New York, Springer-Verlag, 2004. pp. 565)

$$L_s = \frac{\mu N^2 A}{l} \quad (9)$$

where $\mu$ is the permeability of free-space, N, number of turns, A, cross-sectional area of coil, and l is the length of coil. The self-inductance of the lead wire extension $L_1$ is given by (F. W. Grover, *Inductance Calculations*, New York, Dover Publications, Inc. 1973)

$$L_i = 0.002 l_{lead}\left(\ln\frac{2l_{lead}}{r} - 1\right) \quad (10)$$

here $l_{lead}$ refers to the length of the lead wire extension and r is the radius of the wire. The mutual inductance $M_1$ between a parallel lead wire of length $l_{head}$ separation distance d is given by (Grover, et al. supra)

$$M_1 = 0.002 l_{lead}\left[\ln\left(\frac{l_{lead}}{d} + \sqrt{1 + \frac{l_{lead}^2}{d^2}}\right) - \sqrt{1 + \frac{l_{lead}^2}{d^2}} + \frac{d}{l_{lead}}\right] \quad (11)$$

The AMF coil inductance values based on analytical, numerical calculations and experimental measurement are provided in Table 1. For MoM simulation, the solenoid was tuned to resonance at 160 kHz with ~1.2 μF capacitor. The actual capacitor value used in the experimental set up is 1.3 μF.

TABLE 1

| AMF coil electrical properties | | | | | |
|---|---|---|---|---|---|
| Analytical | | Numerical | | Experimental | |
| Inductance | Resistance | Inductance | Resistance | Inductance | Resistance |
| 740 nH | 5.4 mΩ | 738 nH | 4.6 mΩ | 753 nH | 5.97 mΩ |

To determine the effect of dielectric shielding on non-specific heating of the sample, a hollow cylindrical volume with distilled water at 22° C. ($\epsilon_r = 80$ and $\sigma = 0.01$ S/m) was modeled and simulated around the sample volume. The volume averaged specific absorption rate (SAR) in the sample volume and shielding material was calculated to determine the shielding effect. Power applied to coil was held constant at 8 kW (peak) in both cases.

Gel Phantom

Experimental validation of the shielding effect was done with 1% w/w agar gel phantoms (Sigma Aldrich, St. Louis, Mo.) containing 0.035 M NaCl prepared in the 50-ml centrifuge tubes. Three optical temperature probes were placed into the gel. One was placed into the radial center of the phantom (core) whereas the other two were placed 5 mm from the opposing side walls of 50 ml tubing at the center of the solenoid to monitor temperature.

Temperature measurements were performed in the phantom with and without the shielding, and with shielding+active regulation (flowing temperature-controlled water through shield). To test the effect shielding and active thermal regulation, water was pumped through the device at 20° C. Water entered the tube from the bottom and exited through the upper connector to ensure sufficient mixing.

Mice

Six male BALB/c nu/nu mice (Harlan Labs, Indianapolis, Ind.) were used in this study. All were 5 to 8 weeks old and weighed 21 to 26 g (mean 22±2 g) prior to treatment. They were maintained according to Johns Hopkins University School of Medicine guidelines on a normal diet, ad libitum. All methods described were approved by the Institutional Animal Care and Use Committee (IACUC).

Each mouse was anesthetized by an intraperitoneal injection of a ketamine (100 mg/kg body mass)/xylazine (10 mg/kg) solution in 0.9% saline. The solution was filtered through a 0.2 μm filter. Sufficient anesthesia was determined by the lack of a reflexive response when a hind paw was lightly compressed.

After each mouse was anesthetized four fiber optic temperature probes were positioned: one in the rectum, two sub-cutaneous (s.c.) in the following locations: i) the dorsal thorax, and ii) the other contralateral thorax to mimic the probe testing locations done in the agar (top, core, bottom). The fourth and final probe was taped to the skin on the ventral surface, level with the s.c. probes. The s.c. probes were placed with a the aid of a 19-guage 1.5 inch hypodermic needle. After the probes were in place, each mouse was placed into custom-cut plastic mouse holder fashioned from a 50-mL centrifuge tube.

Each mouse was inserted into the shielded chamber and the probes were aligned with the center of the solenoid. The non-shielding and shielding were tested again under the same water (20° C.) conditions as with the gel phantoms. However, for shielding+active regulation, the water temperature was maintained at 35° C. Temperature conditions for each probe were recorded using FISO software for 20 minutes of AMF treatment and for a brief "cool-down" period after the AMF were removed.

SAR analysis was performed to analyze the shielding effect in mice. The SAR is proportional to the temperature gradient at initial time period. The SAR in the sample volume is given by, $$SAR = C\frac{dT}{dt}, \quad (12)$$

here C is the specific heat of the sample volume, and $$\frac{dT}{dt}$$

is the initial slope of the temperature rise curve. The temperature rise during the application of power to AMF coil was plotted as function of time, and initial slopes of the curves were used to estimate the SAR of the agar gel phantom. Mouse specific heat was estimated by calculating the mean specific heat value of seven tissue and organ types as reported by (Trakic, et al. supra). The organs and tissues used in this estimate comprise: Liver, spleen, blood, muscle, skin, lung, and intestines. The mean mass of mice (22 g) was also used.

Dielectric Shield Thickness on Shielding Effect

The dielectric shielding effect as a function of shield thickness was numerically analyzed by increasing the dielectric shield thickness around a 28 mm diameter, 40 mm long cylindrical sample volume. The sample was placed inside a 60 mm diameter, 32 mm long, solenoid coil with four turns as tuned at 160 kHz and 8 kW (peak) power was applied to the coil. The volume average SAR in the sample volume is calculated as the dielectric shield thickness was increased.

Results

The numerical simulation method suited for EM calculations at AMF frequency was validated by determining the solenoid coil inductance within 3% deviation from the actual measured inductance and analytical calculations as listed on Table 1. Table 2 lists the analytically and numerically calculated field values and experimentally measured field values for the applied voltages on the solenoid coil.

TABLE 2

AMF coil voltage and magnetic field

| Voltage (peak) | Analytical Field (Oe) | Numerical Field (Oe) | Experimental Field (Oe) |
|---|---|---|---|
| 137 | 204 | 216 | 190 |
| 275 | 410 | 440 | 421 |
| 410 | 612 | 653 | 649 |
| 535 | 798 | 854 | 862 |
| 690 | 1030 | 1093 | 1084 |

In FIG. 3, (a) and (b) show the magnetic field maps and (c) and (d) show the field profile along the z direction at the middle across the x-z plane in the dielectric region/s within the AMF coil, without shielding material and with shielding material, respectively for 8 kW input power to the coil. As shown in FIG. 3, the magnetic field within the sample volume is essentially not affected by the shielding material around the sample volume.

Figure 4:
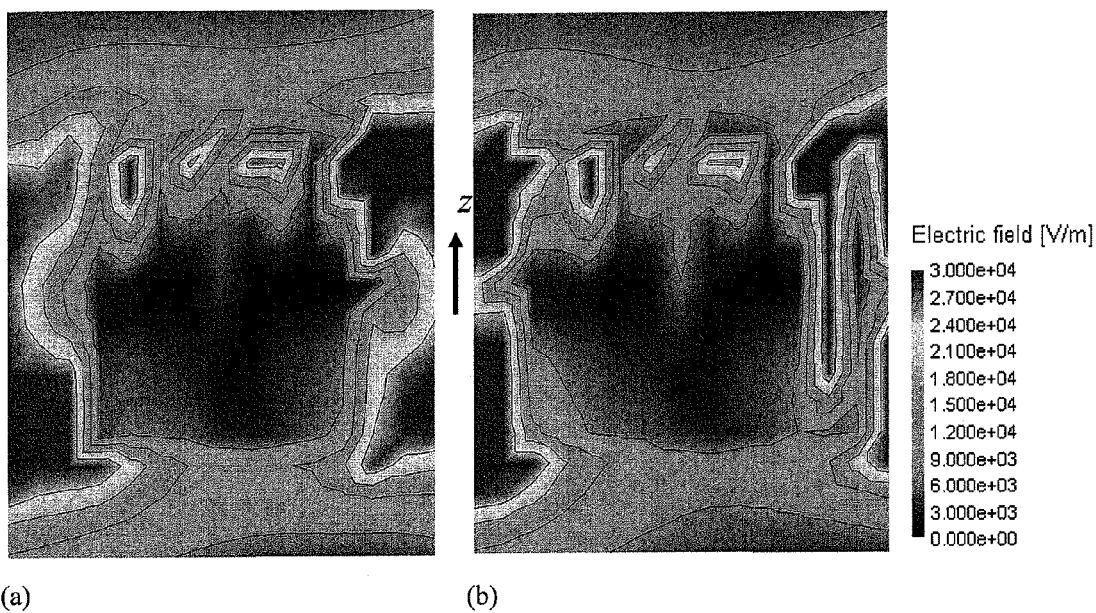
FIG. 4 shows the electric field map across the (x-z plane) in the unshielded (a) and shielded (b) dielectric sample volume for 8 kW (peak) input power to AMF coil.

FIG. 4 show the E field map across the dielectric sample volume under unshielded (a) and shield (b) conditions for 8 kW input power into the coil.

Figure 5A:
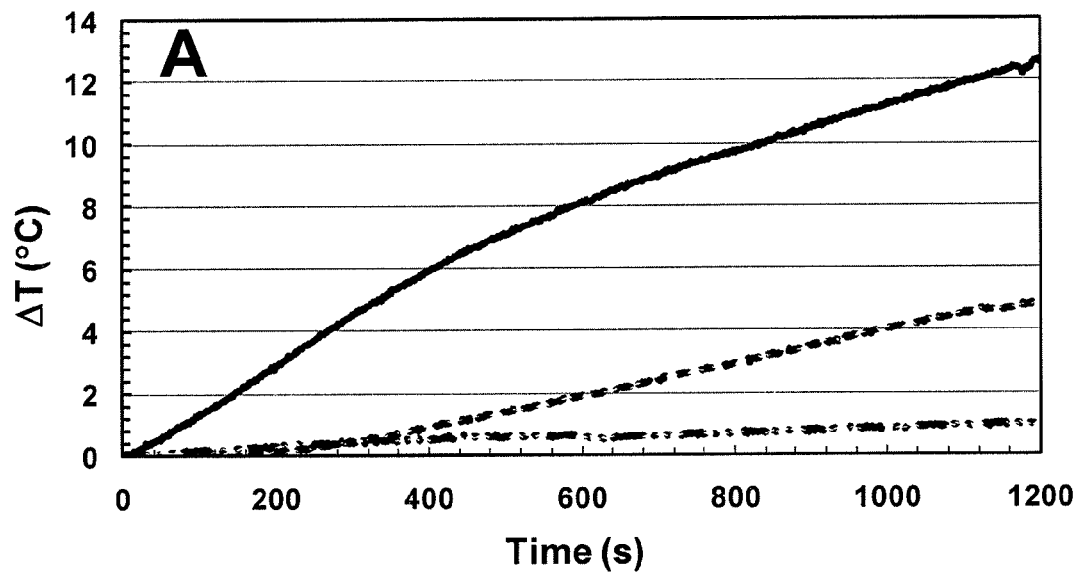
FIG. 5 shows corrected temperature change as measured in the thorax (A) and rectum (B) for, mouse exposed to RF with no dielectric shielding, i.e. unshielded (solid line); mouse exposed to RF with shielding but no diffusion, i.e. shielded (dashed line); and, mouse exposed to RF with both shielding and diffusion (dash-dot-dot). Subcutaneous thoracic temperatures were averaged for both left and right side. In all cases, the temperature change for each temperature probe was calculated from measured temperatures, and the total change of temperature was estimated after subtracting temperature changes obtained from sham controls.
Figure 5B:
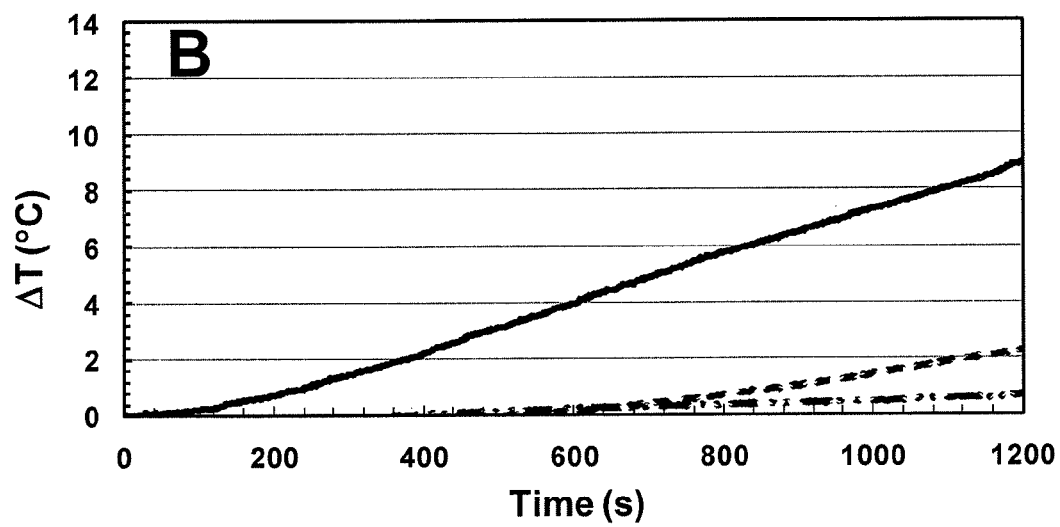

Temperature data obtained from mice occupying the sample volume with and without shielding are shown in FIGS. 5(a) & (b), respectively.

Figure 6:
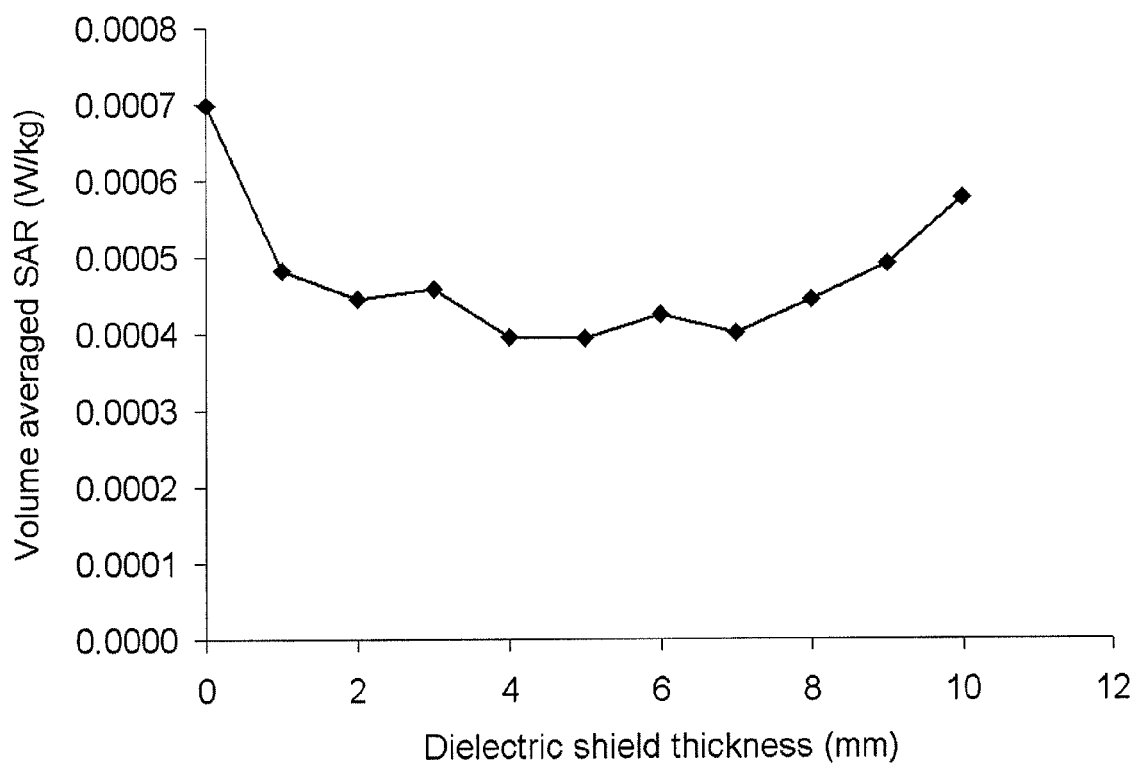
FIG. 6 Shows the volume averaged SAR in the cylindrical (28 mm diameter, 40 mm long) sample volume inside a 60 mm diameter, 32 mm long solenoid with 4 turns. Applied peak power to coil is 8 kW.

Computer simulations predict that the volume averaged SAR value in the sample volume is reduced by approximately by a factor of two by introducing a dielectric shielding material around the sample volume as shown in FIG. 6.

DISCUSSION AND CONCLUSION

By nature solenoids also generate substantial electric fields that can deposit significant amount of energy to a sample, thereby increasing the non-specific power deposition that may degrade the effectiveness of the magnetic fields for some applications. For magnetic nanoparticle-based therapies, AC magnetic fields are used to activate the particles concentrated in specific areas of tissue. Non-specific heating of tissues outside the treatment region can be reduced with shielding technology that absorbs power generated by E-fields and that is simultaneously transparent to the B-fields.

We demonstrate that water effectively allows the magnetic fields to permeate to the sample while simultaneously protecting the sample from excessive non-specific heating. The result is a significant reduction in the deposited power that would otherwise cause increased non-specific heating in the sample volume of interest. The MoM simulations using VEP technique predicted a factor of two reduction in the volume averaged SAR in a cylindrical sample volume of 28 mm when shielded by a 4 mm thick hollow cylindrical dielectric shielding jacket. Experiments with agar gel phantom support the computer simulation results. The experimental results also gave an average two-fold reduction in the SAR.

As shown in FIGS. 3 and 4 an optimal thickness water jacket effectively protects the sample from overheating while allowing the magnetic fields to permeate across it. The numerical simulation method suited for EM calculations at AMF frequency was validated by determining the solenoid coil inductance within 3% deviation from the actual measured inductance. The MoM simulations using VEP technique predicted a factor of two reduction in the volume averaged SAR in a cylindrical sample volume of 28 mm when shielded by a 4 mm thick hollow cylindrical dielectric jacket. It was experimentally verified on an agar gel phantom by temperature measurements while AMF heating was done on with and without the dielectric shielding jacket. FIG. 6 shows the effect of the shield thickness on the shielding efficiency by plotting the volume averaged SAR as a function of shield thickness. The volume averaged SAR value in the sample volume reaches minimum for shield thickness between 4 and 6 mm.

The introduction of dielectric shielding around the sample volume for AMF-nanoparticle therapy at this frequency is an effective way to significantly reduce non-specific heating and its adverse effects. The non-specific power deposition in the lossy sample volume could be further reduced by active regulation by circulating the distilled water in the shielding jacket, where we have shown a reduction of SAR in the agar phantom. We have successfully demonstrated the beneficial effects of a water (high dielectric) shield to reduce non-specific power deposition by numerical EM simulations and experimental validation in a physiologically similar agar gel phantom and in an in vivo setting involving a mouse model with targeted magnetic nanoparticle assisted TEMT.

The embodiments illustrated and discussed in this specification are intended only to teach those skilled in the art the best way known to the inventors to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of exposing a region of interest of an object, animal or person to an alternating magnetic field, comprising:

generating electromagnetic radiation having a predetermined frequency and amplitude;
arranging said object, animal or person to be exposed to at least an alternating magnetic field component of said electromagnetic radiation;
disposing the object, animal or person within an exposure volume defined by a rigid wall of a shield, such that the shield is disposed between the object, animal, or person and a source of the electromagnetic radiation, and such that the shield reduces power deposition to regions outside of said region of interest of said object, animal or person when being exposed to said alternating magnetic field;
wherein said shield comprises a material having a sufficient thickness and arrangement to reduce power deposition to at least regions outside of said region of interest of said object, animal or person during exposure in said exposure volume, wherein said material of said shield comprises water, and
wherein said source of radio-frequency electromagnetic radiation comprises an electrically conducting coil that winds around at least a portion of said exposure volume defined by said system to provide a solenoid having an inner diameter suitable to accommodate said object, animal or person, and wherein said water of said shield has a thickness of at least about 2% of the inner diameter of said coil and less than about 20% of said coil.

2. A method of exposing an object to an alternating magnetic field according to claim 1, wherein the shield comprises at least one of a liquid metal or metal particles suspended in the water.

3. A method of exposing an object to an alternating magnetic field according to claim 1, further comprising disposing magnetic particles in said object such that at least localized regions of said object are heated through interactions of said alternating magnetic field with said magnetic particles.

4. A method of exposing an object to an alternating magnetic field according to claim 1, wherein said generating electromagnetic radiation generates electromagnetic radiation with a frequency of at least 100 kHz.

5. A system for heating localized regions within a body, comprising:
a source of radio-frequency electromagnetic radiation arranged to provide an alternating magnetic field in an exposure volume defined by said system;
a shield having a rigid wall having an inner and an outer surface, wherein the inner surface of the rigid wall defines the exposure volume, and wherein the shield is arranged between said source of radio-frequency electromagnetic radiation and said exposure volume; and
a plurality of magnetic particles that are suitable to be disposed in said body,
wherein said shield comprises a material having a sufficient thickness and arrangement to attenuate electric field components of said electromagnetic radiation produced by said source by a predetermined amount prior to reaching said exposure volume while permitting magnetic field components of said electromagnetic radiation to pass through with less attenuation than said attenuation of said electric field components, and wherein said shield comprises a material having a sufficient thickness and arrangement to reduce power deposition to at least regions outside of said region of interest of said object, animal or person during exposure in said exposure volume, wherein said material of said shield comprises water,
wherein said alternating magnetic field in said exposure volume is suitable to interact with said magnetic particles to generate a predetermined amount of heat, and
wherein said source of radio-frequency electromagnetic radiation comprises an electrically conducting coil that winds around at least a portion of said exposure volume defined by said system to provide a solenoid having an inner diameter suitable to accommodate said object, animal or person, and wherein said water of said shield has a thickness of at least about 2% of the inner diameter of said coil and less than about 20% of said coil.

6. An apparatus for exposing a region of interest of an object, animal or person to an alternating magnetic field, comprising:
a source of radio-frequency electromagnetic radiation arranged to provide said alternating magnetic field in an exposure volume defined by said apparatus; and
a shield arranged between said source of radio-frequency electromagnetic radiation and said exposure volume,
wherein said shield comprises a material having a sufficient thickness and arrangement to reduce power deposition to at least regions outside of said region of interest of said object, animal or person during exposure in said exposure volume, wherein said material of said shield comprises water, and
wherein said source of radio-frequency electromagnetic radiation comprises an electrically conducting coil that winds around at least a portion of said exposure volume defined by said system to provide a solenoid having an inner diameter suitable to accommodate said object, animal or person, and wherein said water of said shield has a thickness of at least about 2% of the inner diameter of said coil and less than about 20% of said coil.

7. An apparatus for exposing a region of interest of an object, animal or person to an alternating magnetic field according to claim 6, wherein said electrically conducting coil is metal tubing adapted to be connected to a cooling system to circulate coiling fluid through said metal tubing.

8. An apparatus for exposing a region of interest of an object to an alternating magnetic field according to claim 6, wherein said radio-frequency electromagnetic radiation comprises linearly polarized electric and magnetic fields having a frequency between 50 kHz and 1 MHz, and an amplitude of between 10 kA/m and 1,000 kA/m.

9. An apparatus for exposing a region of interest of an object, animal or person to an alternating magnetic field according to claim 6, wherein said material of said shield and a structure and arrangement of said shield are selected such that electric field components of said radio-frequency electromagnetic radiation are attenuated by a predetermined amount prior to reaching said exposure volume.

10. An apparatus for exposing a region of interest of an object, animal or person to an alternating magnetic field according to claim 6, wherein said shield comprises at least one of a liquid metal or metal particles suspended in said water.

11. An apparatus for exposing a region of interest of an object, animal or person to an alternating magnetic field according to claim 6, wherein said shield comprises a fluid containment structure comprising an input port and an output port such that said water can be compelled to flow through said shield.

12. An apparatus for exposing a region of interest of an object, animal or person to an alternating magnetic field according to claim 6, wherein said source of radio-frequency electromagnetic radiation is adapted to provide electromagnetic radiation with a frequency of at least 100 kHz.

13. An apparatus for exposing a region of interest of an object, animal or person to an alternating magnetic field according to claim 6, wherein said source of radio-frequency electromagnetic radiation has an applied voltage of at least 500 V.

\* \* \* \* \*